(12) United States Patent
Zhao et al.

(10) Patent No.: US 11,603,836 B2
(45) Date of Patent: Mar. 14, 2023

(54) MICROFLUIDIC PUMP-BASED INFUSION ANOMALY STATE DETECTION AND CONTROL SYSTEM

(71) Applicant: Healtell (Guangzhou) Medical Technology Co., Ltd., Guangdong (CN)

(72) Inventors: Hanguang Zhao, Guangdong (CN); Yibo Xu, Guangdong (CN)

( * ) Notice: Subject to any disclaimer, the term of this patent is extended or adjusted under 35 U.S.C. 154(b) by 112 days.

(21) Appl. No.: 17/280,865

(22) PCT Filed: May 10, 2019

(86) PCT No.: PCT/CN2019/086412
§ 371 (c)(1),
(2) Date: Mar. 26, 2021

(87) PCT Pub. No.: WO2020/062882
PCT Pub. Date: Apr. 2, 2020

(65) Prior Publication Data
US 2022/0003230 A1    Jan. 6, 2022

(30) Foreign Application Priority Data
Sep. 29, 2018   (CN) .......................... 201811145948.0

(51) Int. Cl.
*F04B 51/00*    (2006.01)
*A61M 5/168*    (2006.01)
(Continued)

(52) U.S. Cl.
CPC ......... *F04B 51/00* (2013.01); *A61M 5/16854* (2013.01); *F04B 43/043* (2013.01);
(Continued)

(58) Field of Classification Search
CPC ...... F04B 43/043; F04B 43/046; F04B 49/06; F04B 49/065; F04B 49/08; F04B 49/10;
(Continued)

(56) References Cited

U.S. PATENT DOCUMENTS 4,846,792 A * 7/1989 Bobo, Jr. .......... A61M 5/16859
128/DIG. 13
5,078,682 A * 1/1992 Miki .................. G05D 16/2066
128/DIG. 13
(Continued)

*Primary Examiner* — Charles G Freay
(74) *Attorney, Agent, or Firm* — Prakas Nama; Global IP Services, PLLC

(57) ABSTRACT

The present invention provides a microfluidic pump-based infusion anomaly state detection and control system, comprising: a microfluidic pump chip configured to control the vibration of an actuating device to output a liquid; a pressure sensor located in a pipeline behind the outlet of the microfluidic pump chip and configured to sense the change of the pressure of the liquid output by the microfluidic pump chip to output an electric signal; a signal conditioning circuit configured to perform signal conditioning on the electric signal to obtain a conditioned electric signal; a signal acquisition circuit configured to convert the conditioned electric signal from an analog signal into a digital signal; a signal processing unit configured to determine the working state of the microfluidic pump chip and the working state of an infusion pipeline according to the digital signal, and to send a signal to an alarming unit when an anomaly is found; the alarming unit configured to alarm according to the signal; and a control drive unit configured to adjust the output state of the microfluidic pump chip according to the output of the signal processing unit. The present invention can precisely control a microfluidic pump chip and accurately detect the anomaly state of the microfluidic pump chip and alarm in time.

8 Claims, 5 Drawing Sheets

(51) Int. Cl.
  *F04B 49/10* (2006.01)
  *F04B 43/04* (2006.01)
  *F04B 49/08* (2006.01)
  *F04B 49/06* (2006.01)
  *G01L 7/08* (2006.01)

(52) U.S. Cl.
  CPC .............. *F04B 49/06* (2013.01); *F04B 49/08* (2013.01); *F04B 49/10* (2013.01); *A61M 2005/16863* (2013.01); *A61M 2205/18* (2013.01); *A61M 2205/3331* (2013.01); *F04B 43/046* (2013.01); *F04B 2205/05* (2013.01); *F04B 2207/70* (2013.01); *G01L 7/08* (2013.01)

(58) Field of Classification Search
  CPC . F04B 51/00; F04B 2205/05; A61M 5/16854; A61M 2005/16863; A61M 2005/18; A61M 2005/3331; G01L 7/08
  See application file for complete search history.

(56) References Cited

U.S. PATENT DOCUMENTS

| | | | |
|---|---|---|---|
| 5,190,522 A * | 3/1993 | Wojcicki | A61M 5/16859 604/118 |
| 5,276,610 A * | 1/1994 | Maeda | A61M 5/16854 128/920 |
| 10,874,793 B2 * | 12/2020 | Oruklu | A61M 5/16854 |
| 11,077,248 B2 * | 8/2021 | Juretich | G01R 33/00 |
| 2005/0225201 A1 * | 10/2005 | Vogeley | F04B 43/046 310/317 |

* cited by examiner

MICROFLUIDIC PUMP-BASED INFUSION ANOMALY STATE DETECTION AND CONTROL SYSTEM

BACKGROUND OF THE INVENTION

The invention relates to the technical fields of medical treatment, biology, chemistry, agriculture, beauty treatment, and sanitary ware, and in particular to an infusion abnormality detection and control system for microfluidic pump.

Being an important constituent of microfluidic technology, microfluidic pump chip has a good prospect in the field of medical applications, biology, chemistry, agriculture, beauty treatment, sanitary ware, etc. due to its simple structure, lightness, thinness, low frequency operation, and low power consumption etc. In actual use, a corresponding abnormality detection and control system is a very important part of the whole system. In particular, for applications that have high requirements for safety and stability, various status of the equipment during the operation process must be monitored to prevent potential risks caused by abnormalities such as pipeline blockage, empty storage container, pump chip failure, bubble retention, and fluid leakage.

At present, most of the electronic injection pumps on the market have a mechanical structure that feeds fluid by driving a piston. By detecting the resistance of the push rod, different working status of an electronic injection pump can be determined. However, due to piston resistance, sensitivity of this method is not high, and a high accumulative pressure will be imposed on the fluid path, posing a certain degree of safety risk due to possible infusion of a large amount of fluid within a short period of time upon blockage clearance.

In addition, there is a kind of silicon-based MEMS (Microelectromechanical systems) microfluidic pump chip that integrates a pressure sensor inside. This solution solves the problem of sensitivity. However, the pressure sensor integrated in the chip detects only the pressure change of the pipeline inside the chip. Yet, abnormal infusion may also occur in the pipeline outside the chip. Therefore, it is not sufficient to detect only the pressure change of the pipeline inside the chip. Different designs of outer pipeline, and even vibration of the infusion tube may affect detection precision and accuracy. Therefore, this solution cannot precisely and accurately detect the abnormal infusion status of the entire system.

BRIEF SUMMARY OF THE INVENTION

In view of the disadvantages of existing microfluidic pump system in abnormality detection and precision control, the present invention provides an infusion abnormality detection and control system for microfluidic pump. The present invention can monitor the working status of the microfluidic pump chip and the feeding pipeline in real time, and stop or adjust an operation of the microfluidic pump chip and send out an alert in time when an abnormal operation is detected.

The infusion abnormality detection and control system for microfluidic pump according to the present invention comprises:

a microfluidic pump chip that outputs liquid by controlling vibration of an actuating device;

at least one pressure sensor, at least one of which installed at a pipeline subsequent to an outlet of the microfluidic pump chip; the at least one pressure sensor senses a change in pressure of the liquid output by the microfluidic pump and outputs an electrical signal; each of said at least one pressure sensor comprises structurally from top to bottom an upper cover, a pressure-sensitive material a barrier layer, a sensing chamber and a lower cover, and a sensing chamber; the sensing chamber is defined by a bottom surface of the barrier layer and a top surface of the lower cover to allow the liquid output from the microfluidic pump to pass through; the barrier layer is a flexible material which isolates the liquid and deforms in response to a pressure of the liquid so as to transmit the pressure of the liquid to the pressure-sensitive material;

a signal regulating circuit that regulates the electrical signal to obtain a regulated electrical signal;

a signal collecting circuit that converts the regulated electrical signal from an analog signal to a digital signal;

a signal processing unit that determines working status of the microfluidic pump chip and infusion pipeline according to the digital signal; the signal processing unit comprises an analysis module, a determination module and an output module; the analysis module analyzes the digital signal to obtain a liquid pressure value represented by the electric signal; the determination module determines which working status of the microfluidic pump chip and the infusion pipeline are in according to the fluid pressure value; when an abnormality is detected the output module sends out the alert signal to the alarm unit; the abnormality is pipeline blockage, empty storage container, pump chip failure, bubble retention, or fluid leakage;

said alarm unit sends out an alert according to the signal received from the signal processing unit; and a driving control unit that adjusts an output status of the microfluidic pump chip according to outputs from the signal processing unit.

Preferably, the microfluidic pump chip comprises the actuating device, a pump chamber, a connecting mechanism, an inlet valve and an outlet valve; the pump chamber allows the liquid to pass through; and the actuating device is used as a driving source.

Preferably, the microfluidic pump chip and said at least one pressure sensor is connected through the pipeline; the pipeline is a flow channel designed to reduce or eliminate interference with the liquid due to external factor and sudden change of resistance.

Preferably, the at least one pressure sensor is installed in an independent chamber, or integrated to the pipeline to form part of the pipeline.

Preferably, the at least one pressure sensor comprises a plural number of pressure sensors, provided in front of an input of the microfluidic pump chip, in the microfluidic pump chip, and subsequent to the outlet of the microfluidic pump chip respectively in order to monitor an entire path of the liquid.

Preferably, an alert of the alarm unit is a vibration alert, a sound alert, a lighting alert, or a screen displayed alert.

Preferably, the alarm unit further comprises a wireless transmission module.

Preferably, a noise filtering module for filtering out motion noises interference is provided in the signal processing unit.

Preferably, the noise filtering module filters motion noises by adopting closed-loop control principle or the noise filtering module uses a motion sensor to filter motion noises, or the noise filtering module is embodied as a dual pressure sensor.

Preferably, the driving control unit adjusts parameters of the driving signal output to the microfluidic pump chip according to the outputs from the signal processing unit; the parameters of the driving signal comprises a voltage of the driving signal, a frequency of the driving signal, and a duty cycle of the driving signal.

The present invention has the following beneficial effects; by using the abnormality detection and control system according to the present invention, the microfluidic pump chip can be precisely and accurately controlled, and its abnormal status can be precisely and accurately detected and an alert can be sent out in time.

DETAILED DESCRIPTION OF THE INVENTION

The present invention is further described in detail below through an embodiment. The embodiment as described below is given only for better understanding of the technical contents of the present invention, and should not be considered limiting the scope of the protection of the present invention.

A structure of the infusion abnormality detection and control system for microfluidic pump according to the present invention will be described in detail below with reference to the figures.

Figure 1:
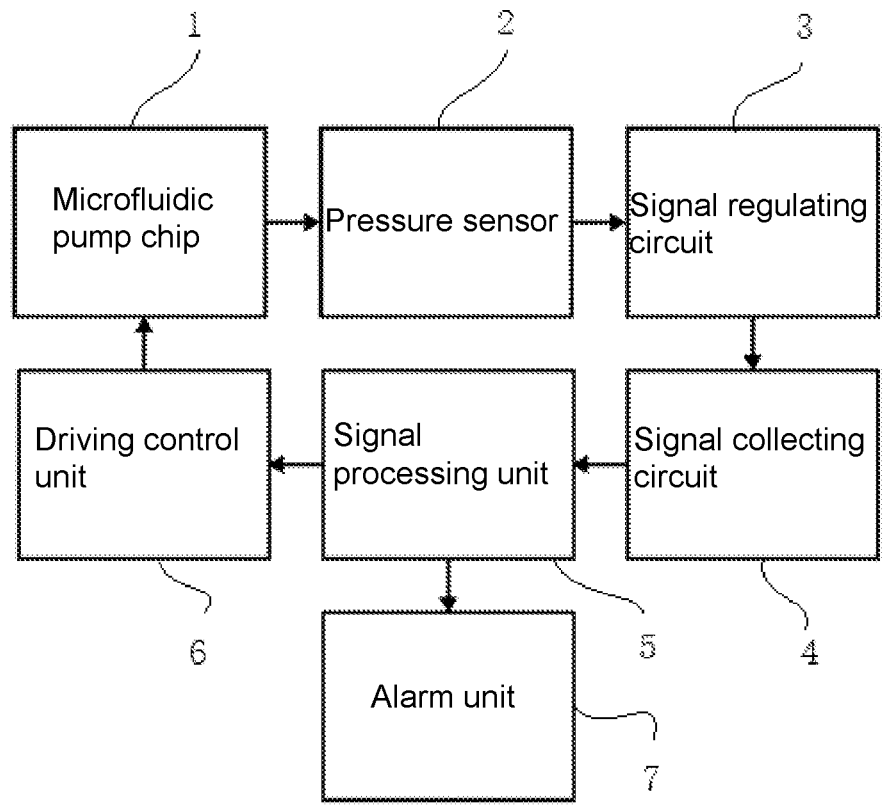
FIG. 1 is a schematic structural view of the infusion abnormality detection and control system for microfluidic pump according to an embodiment of the present invention.

As shown in FIG. 1, an infusion abnormality detection and control system for microfluidic pump according to an embodiment of the present invention comprises a microfluidic pump chip 1, a pressure sensor 2, a signal regulating circuit 3, a signal collecting circuit 4, a signal processing unit 5, a driving control unit 6 and an alarm unit 7. The above components are described in detail below.

Figure 2:
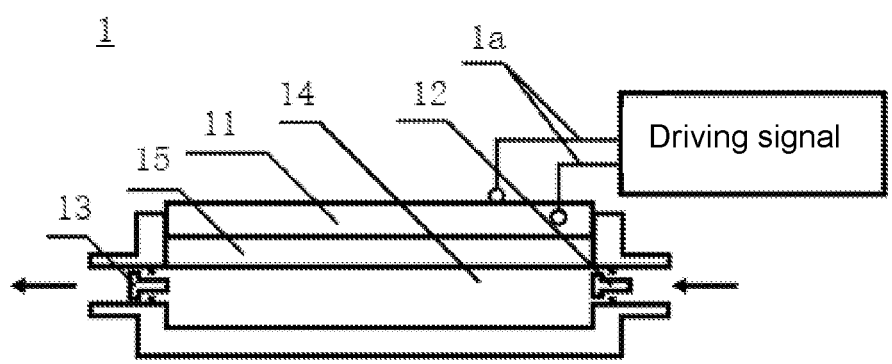
FIG. 2 is a schematic structural view of the microfluidic pump according to an embodiment of the present invention.

The microfluidic pump chip 1 outputs liquid by controlling vibration of an actuating device. A structure of the microfluidic pump chip 1 mainly formed by the actuating device 11, a pump chamber 14, a connecting mechanism 15, an inlet valve 12 and an outlet valve 13 is shown in FIG. 2. The microfluidic pump chip 1 uses the actuating device 11 as a driving source; the actuating device 11 generates vibration upon a driving signal output by the driving control unit 6. The actuating device can be but not limited to piezoelectric ceramic, magnetostrictive device, thermostrictive device, and shape memory alloy. The microfluidic pump chip 1 is connected to the driving control unit 6 through a first wire group 1a. When the driving signal generated by the driving control unit 6 is loaded onto the microfluidic pump chip 1, the actuating device 11 vibrates, and a volume of the pump chamber 14 is directly or indirectly changed through the connecting mechanism 15. Also, the inlet valve 12 and the outlet valve 13 take turns to open and close in order to output liquid. The arrow in FIG. 1 indicates a flow direction of the liquid, and the pump chamber 14 is provided for the flow of the liquid.

Figure 3:
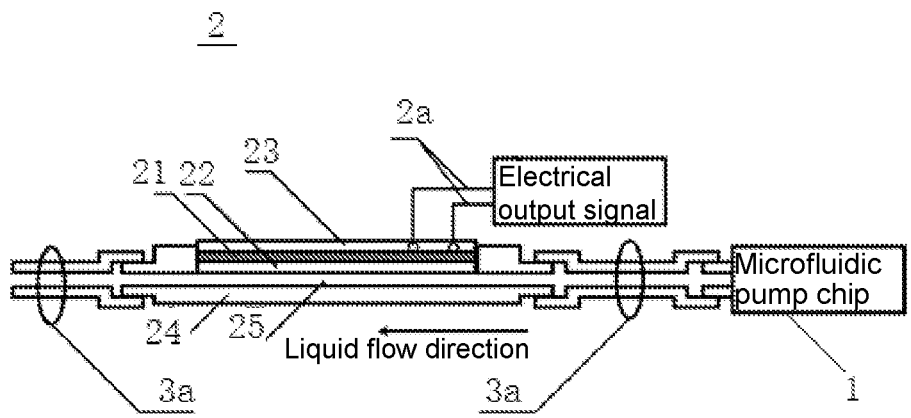
FIG. 3 is a schematic structural view of the pressure sensor according to an embodiment of the present invention.

The pressure sensor 2 is installed at an outlet of the microfluidic pump chip 1, and is connected to the microfluidic pump chip 1 through a pipeline 3a. A structure of the pressure sensor 2 structurally comprises from top to bottom an upper cover 23, a pressure-sensitive material 21, a barrier layer 22, a sensing chamber 25, and a lower cover 24, as shown in FIG. 3. The sensing chamber 25 is defined by a bottom surface of the barrier layer 22 and a top surface of the lower cover 24 to allow the liquid output from the microfluidic pump to pass through. The liquid is output from the microfluidic pump chip 1 and flows to the pressure sensor 2 through the pipeline 3a and then passes through the sensing chamber 25 of the pressure sensor 2. The pipeline 3a is a specially designed flow channel, which can reduce or eliminate interference with the liquid due to external factor and the sudden change of resistance. Said special design of the pipeline includes but not limited to special capillary paths, fluid resistance devices and pressure smoothing devices. The pressure sensor 2 is connected to the pipeline 3a. When the liquid flows through the sensing chamber 25, a change in pressure of the liquid acts on the pressure-sensitive material 21 through the barrier layer 22. The barrier layer 22 is a flexible material which can isolate the liquid but can slightly deform in response to the pressure of the liquid, so as to transmit the pressure to the pressure-sensitive material 21. The pressure-sensitive material 21 is a special material; when the pressure-sensitive material 21 is subject to mechanical deformation, such as pressurizing, stretching, shearing, and twisting, there will be changes in its electrical properties. The electrical properties include but are not limited to resistance, capacitance, inductance, and electrical charge. The pressure-sensitive material 21 of the pressure sensor 2 is a varistor. When the pressure-sensitive material 21 senses a pressure, its electrical properties change. Further, since the lower cover 24 is made of rigid material, a size of the sensing chamber 25 will not change significantly under different pressures. Therefore, the pressure acting on the pressure-sensitive material 21 can precisely and accurately reflect the pressure from the liquid. The pressure sensor 2 and the signal regulating circuit 3 are connected through a second wire group 2a, so that the electrical signal is transmitted to the signal regulating circuit 3.

As mentioned above, the microfluidic pump chip 1 transports liquid based on pressure difference. Under the effect of the driving signal, the pump chamber 14 expands and contracts alternately, while the inlet valve 12 and outlet valve 13 also take turns to open and close, and hence, the liquid is transported by means of changes in pressure. Therefore, a change of an internal pressure of the liquid can reflect different status of the microfluidic pump chip.

The signal regulating circuit 3 is used for conversion, amplification, filtering, and impedance matching of the changed electrical properties from the pressure sensor 2 to obtain a regulated electrical signal. The pressure sensor 2 has the pressure-sensitive material 21 which changes the electrical properties thereof when under pressure, and a first step is to convert the change of the electrical properties into a change of a voltage signal through a conversion circuit. A resistance of the varistor (an embodiment of the pressure-sensitive material 21) changes when under pressure, and the conversion circuit thereof converts the change in resistance into a change in voltage signal via Wheatstone bridge. Alternatively; the varistor can also be directly used as one of the resistors of an operational amplifier circuit to achieve amplification and voltage conversion at the same time.

The pressure sensor 2 of the present invention may also be an optical pressure sensor. The main principle of an optical pressure sensor is that pressure acts on optical fibers or optical gratings to deflect the refraction of light or change the light intensity, and then convert the optical signal into an electrical signal through a photosensitive material, thereby obtaining a value of pressure. In this embodiment, no corresponding conversion circuit is required.

The voltage signal is often a weak signal, and requires amplification through a signal amplifier circuit so that the amplified voltage signal falls within a measurement range of the subsequent signal collecting circuit. A signal filtering circuit of the signal regulating circuit is mainly used to filter out noises, so that only signals at a certain operating frequency are allowed to pass. An impedance matching circuit of the signal regulating circuit is used to match a sensor output impedance and an input impedance of the subsequent signal collecting circuit so as to prevent signal distortion. The signal regulating circuit 3 can use any other known circuits that can achieve signal regulation.

The signal collecting circuit 4 is used to convert the regulated electrical signal from an analog signal to a digital signal. Specifically, the signal collecting circuit 4 can be, for example, an A/D converter.

Figure 4:
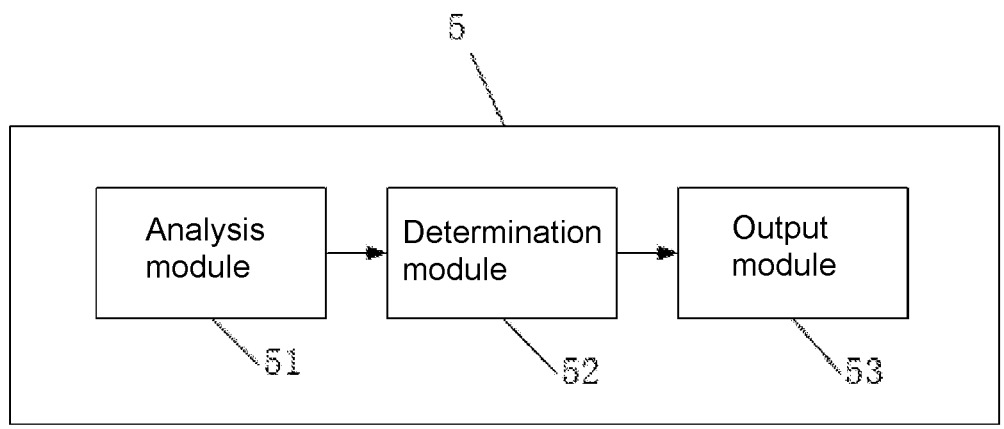
FIG. 4 is a schematic structural view of the signal processing unit according to an embodiment of the present invention.

The signal processing unit 5 is used to determine working status of the microfluidic pump chip and the infusion pipeline according to the digital signal output by the signal collecting circuit 4, and control the microfluidic pump chip to adjust its output characteristics by way of for example regulating driving voltage, driving waveform frequency, and waveform duty through the driving control unit 6. When faults and abnormalities such as blockage or pump failure are detected, adjust or stop operation of the entire microfluidic pump chip, and then send out an alert. Specifically, as shown in FIG. 4, the signal processing unit 5 comprises an analysis module 51, a determination module 52 and an output module 53.

Wherein, the analysis module 51 analyzes the digital signal through an algorithm to obtain a liquid pressure value represented by the electric signal. A person skilled in the art can use any known algorithms or methods to perform the above analysis.

The determination module 52 determines which working status of the microfluidic pump the liquid pressure value corresponds to. The microfluidic pump chip 1 is a chip that enables timed and fixed amount of liquid output, therefore when the liquid passes through the pipeline and being infused, a pressure change of the liquid is represented by a regularly patterned curve. Therefore, characteristics of the change in pressure value with time can correspond to different working status of the microfluidic pump chip and the pipeline, specifically as described in detail below.

When pipeline blockage occurs, each time the microfluidic pump chip operates, there will be an increase in pressure, but a curve representing pressure attenuation is obviously less drastic, and pressure continues to increase when static pressure is analyzed.

When the container is empty, negative pressure will develop in the container, and the negative pressure will offset the pressure generated by the output of the microfluidic pump chip. Therefore, pressure signal will reflect a trend of gradual decrease until eventually it becomes a very weak dynamic pressure signal.

When microfluidic pump chip failure occurs, the pressure sensor cannot sense any pressure change generated by the microfluidic pump chip each time the microfluidic pump chip operates, and thus the pressure signal is represented by a constant linear line.

When bubble retention occurs, due to much higher compressibility of air compared with liquid, the change in pressure value will occur within a smaller range than that during normal operation, and characterization of frequency components of the pressure value will also be different. Further, when it is taken into account that an air evacuating process will occur at an initial stage of system operation, a certain window period must exist for the purpose of status monitoring. When bubbles are discharged within the window period, it is determined that there is no bubble retention. An alert is triggered only when bubble discharge continues by exceeding the window period.

When liquid leakage occurs, static pressure value drops slowly. Also, the dynamic pressure change caused by liquid output from the microfluidic pump chip will drop quickly. Further, the trend of dynamic pressure change will be different for locations where liquid leakage occurs.

In addition, the use of pressure sensor as an abnormality detection sensor has a problem of external motion interference. When the system is transported or operates on a moving object, external vibrations will also be considered as pressure changes. The system cannot distinguish whether a pressure change reflects a change in the working status of the liquid pipeline and the pump, or whether the pressure change is caused by external interference. This problem is difficult to overcome in the prior art technical solution using a pressure sensor. In this system of the present invention, a noise filtering module for filtering out motion noises interference is provided.

Figure 7:
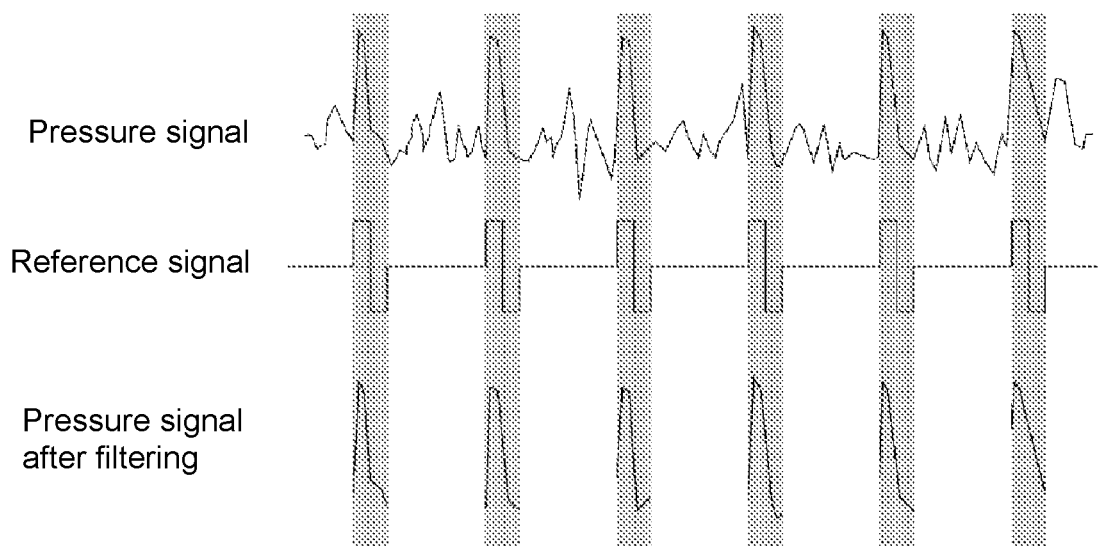
FIGS. 7(a), 7(b) and 7(c) are diagrams of waveforms illustrating how noises are filtered according to three embodiments of the noise filtering module respectively.
Figure 7:
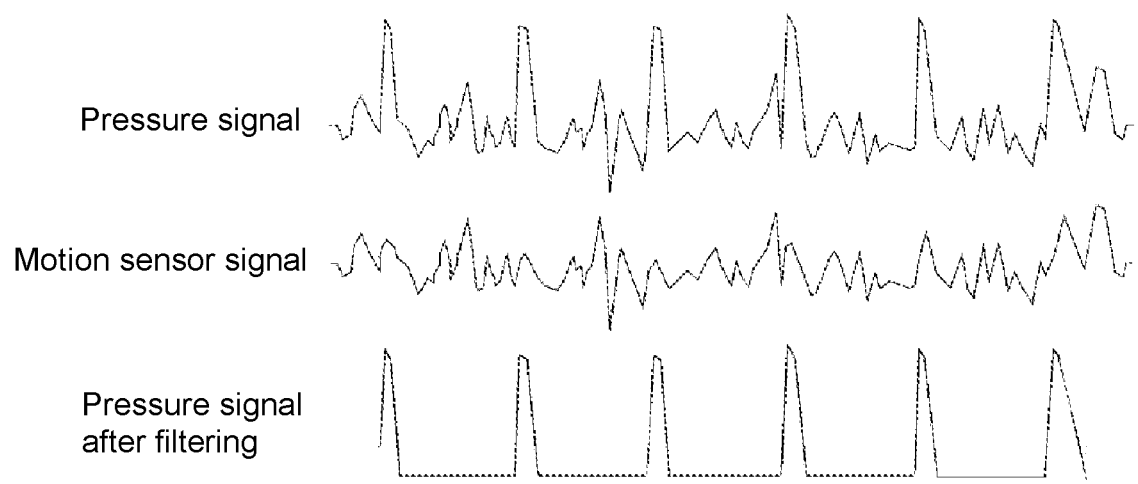
Figure 7:
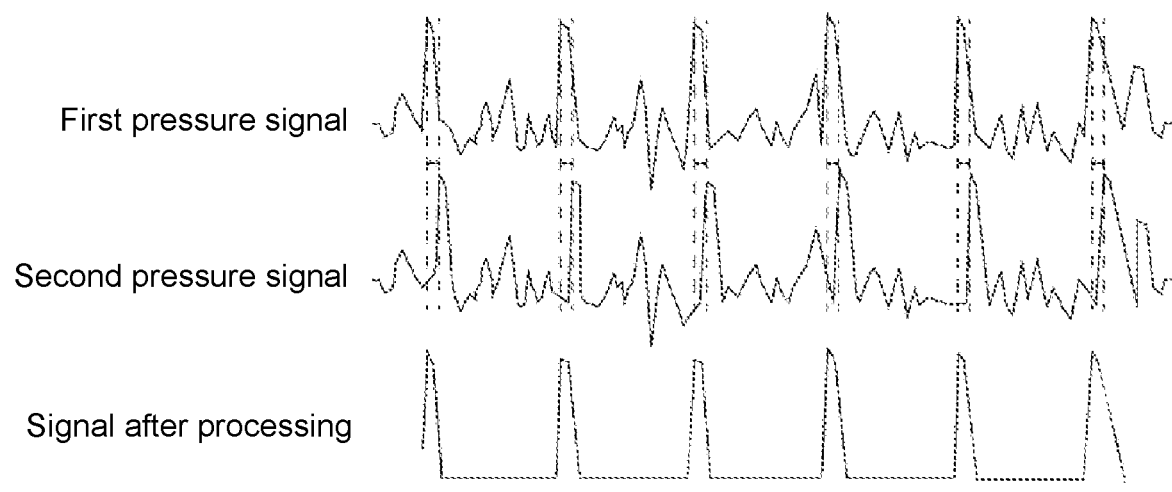

In one embodiment, the noise filtering module filters motion noises by adopting the closed-loop control principle. Specifically, a signal of the closed-loop system of the microfluidic pump is sent from the signal processing unit to the driving control unit. This signal is also used as a reference signal for filtering out motion noises. Align the signal collected by the pressure sensor with the reference signal, and only consider portions the pressure signal when the reference signal is valid. In this way, only portions the pressure signal generated during operation of the microfluidic pump chip is analyzed, and the remaining noises are filtered out, as shown in FIG. 7(a).

In another embodiment, the noise filtering module may also use a motion sensor to filter motion noises. The motion sensor is integrated in the system. After a signal collected by the motion sensor is processed and normalized, it is compared and subtracted from the signal collected by the pressure sensor. In this way, the interferences caused by external movement in the pressure signal are subtracted, and the remaining portions of the pressure signal are those generated when the microfluidic pump chip is operating, as shown in FIG. 7(b).

In another embodiment, the noise filtering module can also be embodied as a dual pressure sensor. Specifically, place two pressure sensors at different positions in the pipeline. Because the relative positions of the two pressure sensors are fixed, a time difference of the two pressure sensors receiving the pressure signal generated by the microfluidic pump and transported in the pipeline is also fixed, so this pressure signal has a fixed phase difference on the two pressure sensors. Interference signals caused by motion affect the two pressure sensors at the same time, so a fixed phase difference does not exist between the two pressure sensors in respect of interference signals. Accordingly, the pressure signal generated by the operation of the microfluidic pump chip can be extracted through a simple signal processing method, as shown in FIG. 7(c).

The above three embodiments of the noise filtering module can be employed at the same time, or one or two of them can be employed.

The output module 53 outputs signals according to the determination result. The output signals mainly comprises a DO signal, an Enable signal and a Sig signal, wherein the DO signal is used to adjust a voltage of the driving signal, the Enable signal is used to switch on or switch off a driving circuit, and the Sig signal is used to adjust a shape, frequency and duty cycle of the driving signal.

The driving control unit 6 is configured to adjust the driving signal output to the microfluidic pump chip 1 according to the output signal to control the output status of the microfluidic pump chip 1. The driving control unit 6 mainly controls the three parameters of the driving signal, namely the voltage of the driving signal, the frequency of the driving signal, and the duty cycle of the driving signal, as mentioned above. These three parameters are used to control the output status of the microfluidic pump chip 1 in real time.

Figure 5:
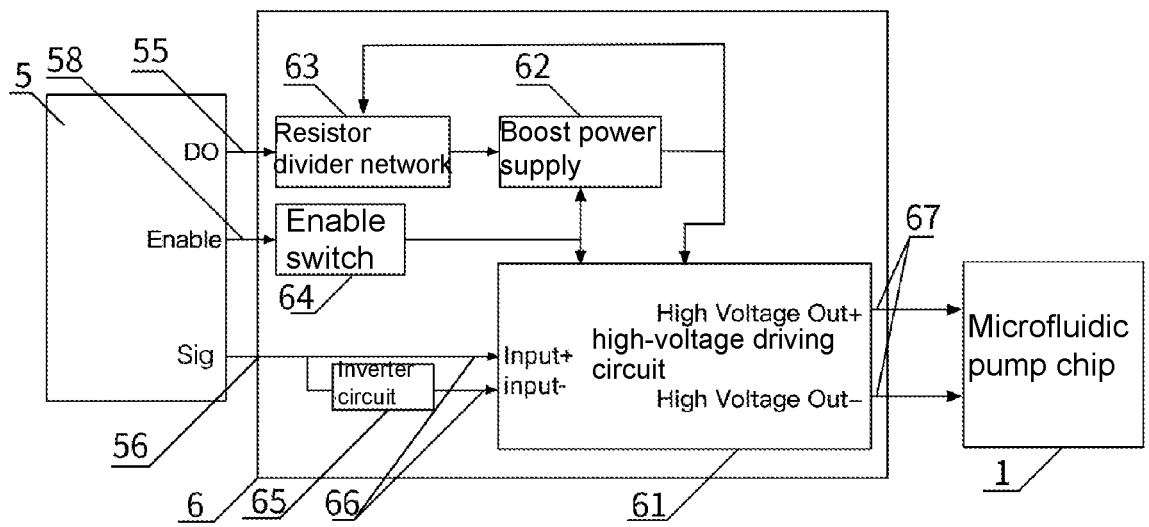
FIG. 5 is a schematic structural view of the driving control unit according to an embodiment of the present invention.
Figure 6:
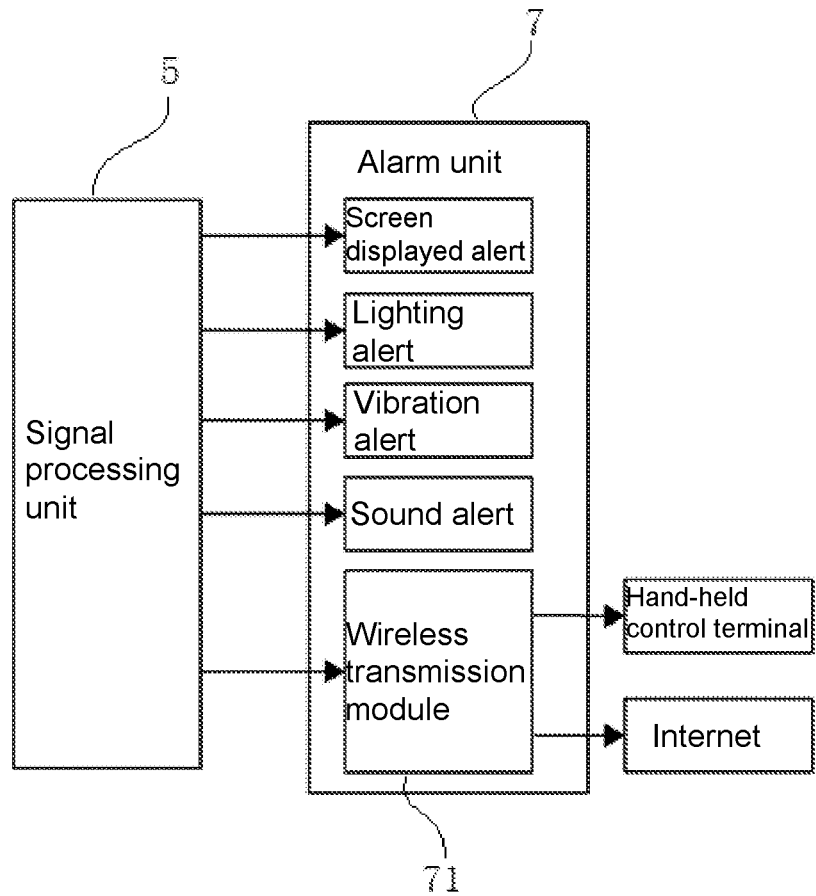
FIG. 6 is a schematic structural view of the alarm unit according to an embodiment of the present invention.

A structural diagram of the driving control unit 6 is shown in FIG. 5. The driving control unit 6 comprises a high-voltage driving circuit 61, a boost power supply 62, a resistor divider network 63, and an enable switch 64 etc. With reference to FIG. 5, controlling of the three parameters of the driving signal according to the three types of output signals (DO signal, Enable signal, and Sig signal) of the output module 53 of the signal processing unit 5 will be described in detail.

An amplitude value of the driving signal is adjusted as follows. The DO signal 55 of the signal processing unit 5 regulates the resistor divider network 63 mainly through two methods; the first method is to use an adjustable resistor, wherein the DO signal directly controls a resistance value of the adjustable resistor; the second method is to output an adjustable voltage, which replaces a signal with a reference voltage of the resistor divider network 63. These two methods can be used alone or in combination to achieve finer-grained control. By regulating the voltage divider resistor network 63 and then through a feedback circuit inside the boost power supply 62, an output voltage of the boost power supply 62 is adjusted, thereby eventually controlling the amplitude value of the driving signal.

The signal processing unit 5 is connected to the enable switch 64 through the Enable signal 58 to control enabling of the boost power supply 62 and the high-voltage driving circuit 61. Specifically, the Enable signal 58 controls the enable switch 64. When the Enable signal is indicated as OFF, a boost circuit of the boost power supply 62 and the high-voltage driving circuit stop operating, so that the output signal of the driving control unit 6 is at 0 level. When the Enable signal is indicated as ON, the boost circuit and the high-voltage drive circuit operate normally.

The Sig signal 56 of the signal processing unit 5 controls the frequency and the duty ratio of the driving signal. The Sig signal is an input reference signal for controlling the driving unit 6; said input reference signal determines a signal frequency and a duty ratio of a first High Voltage Out+/− output signal 65. Sig signal can support any waveforms, including but not limited to square waveform, triangular waveform, and sine waveform etc.

Second High Voltage Out+/− output signals 67 are a pair of signals, which are connected to the actuating device 11 of the microfluidic pump chip 1. In the present embodiment, the pair of signals is a pair of homologous signals with a phase difference of 180 degrees. The pair of signals is generated as follows: The single-ended Sig signal is first divided into two, one of which is connected to an inverter 65, so that the single-ended Sig signal becomes a pair of Input+/− input signals 66 having a mutual phase difference of 180 degrees. When the actuating device 11 of the microfluidic pump chip 1 is connected to the second High Voltage Out+ output signal and the second High Voltage Out− signal of the high-voltage driving circuit, positive level-negative level outputs can be supported. When the actuating device 11 of the microfluidic pump chip 1 is connected to the second High Voltage Out+ output signal and a ground signal, a positive level-ground output can be supported.

Also, the pair of second High Voltage Out+/− output signals 67 can also support asymmetric signals with any phase difference. In this case, the Sig signal changes from a single-ended signal to a double-ended signal, wherein the waveform, phase, and amplitude of each signal can be adjusted according to actual needs, so as to enable the second High Voltage Out+/− output signals in any driving waveform. Accordingly, a more flexible control of the actuating device 11 of the microfluidic pump chip 1 is achieved.

The amplitude value of the driving signal can control a degree of vibration of the actuating device 11 of the microfluidic pump chip 1, thereby changing an output pressure and an amount of infusion by the microfluidic pump chip 1. The frequency of the driving signal corresponds to a number of times the actuating device 11 operates per unit time. The signal duty cycle corresponds to a ratio of operating to non-operating time of the microfluidic pump chip 1. According to the information transmitted by the signal processing unit 5, the driving control unit 6 is controlled to adjust any one or more of the three parameters to control the output status of the microfluidic pump chip 1 in real time.

When the signal processing unit 5 determines that an abnormality occurs, that is, when the microfluidic pump chip or the pipeline is in an abnormal status, the alarm unit 7 is triggered to send out an alert including but not limited to vibration alert, sound alert, lighting alert, and abnormality information displayed on a LCD screen. Also, through a wireless transmission module 71, the abnormal status is reported to a control terminal, so that the control terminal also receives an alert. Moreover, the abnormal status can also be reported to the Internet through the wireless transmission module to realize remote alert.

In addition, the system of the present invention being a closed-loop control system can also achieve certain maintenance functions. When an abnormality is detected, the signal processing unit can adjust the three parameters to change the operation of the pump chip, so as to achieve maintenance. The specific implementations of said maintenance are described as follows:

When a blockage is detected, firstly increase the amplitude value of the driving signal to increase the output pressure of the pump chip. If the pressure sensor detects that the liquid pressure first rises and then continues to decrease, the blockage is removed, and the output pressure returns to the rated value. If the liquid pressure does not decrease, continue to increase the amplitude value of the driving signal until the blockage is removed. If blockage is still detected at the highest amplitude value, maintenance is failed.

When it is detected that there is bubble retention, both the amplitude value and the driving signal frequency of driving signal can be increased simultaneously. Accordingly, the amount of liquid infusion by the microfluidic pump chip increases, and liquid infusion is speeded up to push the bubbles out.

Obviously, a person skilled in this field of art should understand that, the above described embodiment is intended for illustrative purpose only, and should not be considered limiting the present invention. Any changes or variations of the embodiment disclosed above made in accordance with the essence and spirit of the present invention should also fall within the scope defined by the claims of the present invention.

What is claimed is:

1. An infusion abnormality detection and control system for microfluidic pump, comprising:
    a microfluidic pump chip comprising an actuating device; the microfluidic pump chip outputs liquid by controlling vibration of the actuating device;
    at least one pressure sensor, at least one of which installed at a pipeline subsequent to an outlet of the microfluidic pump chip; each of the at least one pressure sensor senses a change in pressure of the liquid output by the microfluidic pump and outputs an electrical signal; each of said at least one pressure sensor comprises structurally an upper cover, a pressure-sensitive material, a barrier layer, a sensing chamber and a lower cover; the sensing chamber is defined by a bottom surface of the barrier layer and a top surface of the lower cover to allow the liquid output from the microfluidic pump to pass therethrough; the barrier layer is a flexible material which isolates the liquid and deforms in response to a pressure of the liquid so as to transmit the pressure of the liquid to the pressure-sensitive material;
    a signal regulating circuit that regulates the electrical signal to obtain a regulated electrical signal;
    a signal collecting circuit that converts the regulated electrical signal from an analog signal to a digital signal;
    a signal processing unit that determines a working status of the microfluidic pump chip and infusion pipeline according to the digital signal; further, when an abnormality of the working status of the microfluidic pump chip is detected, an alert signal is sent out by the signal processing unit to an alarm unit; the abnormality is pipeline blockage, empty storage container, pump chip failure, bubble retention, or fluid leakage;
    said alarm unit sends out an alert according to the alert signal received from the signal processing unit; and
    a driving control unit that adjusts an output status of the microfluidic pump chip according to working status determined by the signal processing unit.

2. The infusion abnormality detection and control system of claim 1, wherein the microfluidic pump chip also comprises a pump chamber, a connecting mechanism, an inlet valve and an outlet valve; the pump chamber allows the liquid to pass therethrough.

3. The infusion abnormality detection and control system of claim 2, wherein the microfluidic pump chip and at least one of said at least one pressure sensor are connected through the pipeline.

4. The infusion abnormality detection and control system of claim 1, wherein the at least one of said at least one pressure sensor is integrated to the pipeline to form part of the pipeline.

5. The infusion abnormality detection and control system of claim wherein said at least one pressure sensor is a plurality of pressure sensors, provided upstream of the input of the microfluidic pump chip, in the microfluidic pump chip, and subsequent to the outlet of the microfluidic pump chip respectively in order to monitor an entire path of the liquid.

6. The infusion abnormality detection and control system of claim 1, wherein the alert of the alarm unit is a vibration alert, a sound alert, a lighting alert, or a screen displayed alert.

7. The infusion abnormality detection and control system of claim 6, wherein the alarm unit further comprises a wireless transmission module.

8. The infusion abnormality detection and control system of claim 1, wherein the driving control unit adjusts parameters of a driving signal output to the microfluidic pump chip according to the outputs from the signal processing unit the parameters of the driving signal comprises a voltage of the driving signal, a frequency of the driving signal, and a duty cycle of the driving signal.

\* \* \* \* \*